(12) United States Patent
Bertram et al.

(10) Patent No.: US 9,719,058 B2
(45) Date of Patent: Aug. 1, 2017

(54) FRAGRANT OIL ENCAPSULATION

(71) Applicants: Papierfabrik August Koehler AG, Oberkirch (DE); Symrise AG, Holzminden (DE)

(72) Inventors: Ralf Bertram, Holzminden (DE); Patrick Ott, Holzminden-Silberborn (DE); Lutz Kühne, Ohlsbach (DE); Claudia Meier, Lichtenau (DE); Julien Schroeder, Strasbourg (FR); Stephan Mahler, Kehl (DE); Claus Jurisch, Durbach (DE)

(73) Assignee: PAPIERFABRIK AUGUST KOEHLER SE, Holzminden (DE)

( * ) Notice: Subject to any disclaimer, the term of this patent is extended or adjusted under 35 U.S.C. 154(b) by 58 days.

(21) Appl. No.: 14/416,212

(22) PCT Filed: Jul. 25, 2013

(86) PCT No.: PCT/EP2013/065768
§ 371 (c)(1),
(2) Date: Jan. 21, 2015

(87) PCT Pub. No.: WO2014/016395
PCT Pub. Date: Jan. 30, 2014

(65) Prior Publication Data
US 2015/0210965 A1    Jul. 30, 2015

(30) Foreign Application Priority Data
Jul. 26, 2012   (EP) ..................... 12178132

(51) Int. Cl.
| | | |
|---|---|---|
| *C11D 3/50* | (2006.01) | |
| *A61K 8/84* | (2006.01) | |
| *C11D 3/37* | (2006.01) | |
| *A61Q 19/00* | (2006.01) | |
| *C11D 17/00* | (2006.01) | |
| *A61K 8/11* | (2006.01) | |
| *A61Q 15/00* | (2006.01) | |
| *A01N 25/28* | (2006.01) | |
| *B01J 13/08* | (2006.01) | |
| *C09B 67/02* | (2006.01) | |
| *A61K 8/49* | (2006.01) | |
| *A61Q 5/02* | (2006.01) | |
| *A61Q 19/10* | (2006.01) | |
| *A61K 8/04* | (2006.01) | |

(52) U.S. Cl.
CPC .............. *C11D 3/505* (2013.01); *A01N 25/28* (2013.01); *A61K 8/044* (2013.01); *A61K 8/11* (2013.01); *A61K 8/4966* (2013.01); *A61K 8/84* (2013.01); *A61Q 5/02* (2013.01); *A61Q 15/00* (2013.01); *A61Q 19/00* (2013.01); *A61Q 19/007* (2013.01); *A61Q 19/10* (2013.01); *B01J 13/08* (2013.01); *C09B 67/0097* (2013.01); *C11D 3/3703* (2013.01); *C11D 17/0039* (2013.01); *A61K 2800/412* (2013.01); *A61K 2800/56* (2013.01); *Y10T 428/2982* (2015.01); *Y10T 428/2984* (2015.01)

(58) Field of Classification Search
None
See application file for complete search history.

(56) References Cited

U.S. PATENT DOCUMENTS

| | | | | |
|---|---|---|---|---|
| 5,011,634 A | * | 4/1991 | Pietsch ................... | B01J 13/18 264/4.7 |
| 8,865,030 B2 | | 10/2014 | Koplin et al. | |
| 9,056,302 B2 | | 6/2015 | Jung et al. | |
| 2002/0031553 A1 | * | 3/2002 | Moyano ............... | A61K 9/5031 424/491 |
| 2010/0261839 A1 | * | 10/2010 | Jung ....................... | B01J 13/14 524/823 |
| 2013/0302392 A1 | * | 11/2013 | Mistry ..................... | A61K 8/11 424/401 |

FOREIGN PATENT DOCUMENTS

| | | |
|---|---|---|
| CN | 101970096 A | 2/2011 |
| CN | 102458641 A | 5/2012 |
| DE | 3818712 | 12/1989 |
| EP | 321750 | 6/1989 |
| WO | 2014016395 | 1/2014 |

OTHER PUBLICATIONS

International Search Report for International Patent Application No. PCT/EP2013/065768, dated Sep. 3, 2013, 2 pages.
The Written Opinion for International Patent Application No. PCT/EP2013/065768, dated Sep. 3, 2013, 6 pages.
International Preliminary Report on Patentability for International Patent Application No. PCT/EP2013/065768, dated Sep. 3, 2013, 7 pages.
First Office Action, including Search Report, for Chinese Patent Application No. 201380039817.3, dated Jan. 25, 2016, 9 pages.

* cited by examiner

*Primary Examiner* — Robert A Wax
*Assistant Examiner* — Danah Al-Awadi
(74) *Attorney, Agent, or Firm* — Westman, Champlin & Koehler, P.A.

(57) ABSTRACT

The invention relates to microcapsules having a particle size distribution that has at least two maxima, wherein the main maximum of the particle size lies in the range of 5 to 100 μm and wherein the volume assumed by the microcapsules that have a particle size less than ¼ of the particle size of the main maximum is greater than approximately 20% of the total volume of the microcapsules.

25 Claims, 11 Drawing Sheets

Figure 1:
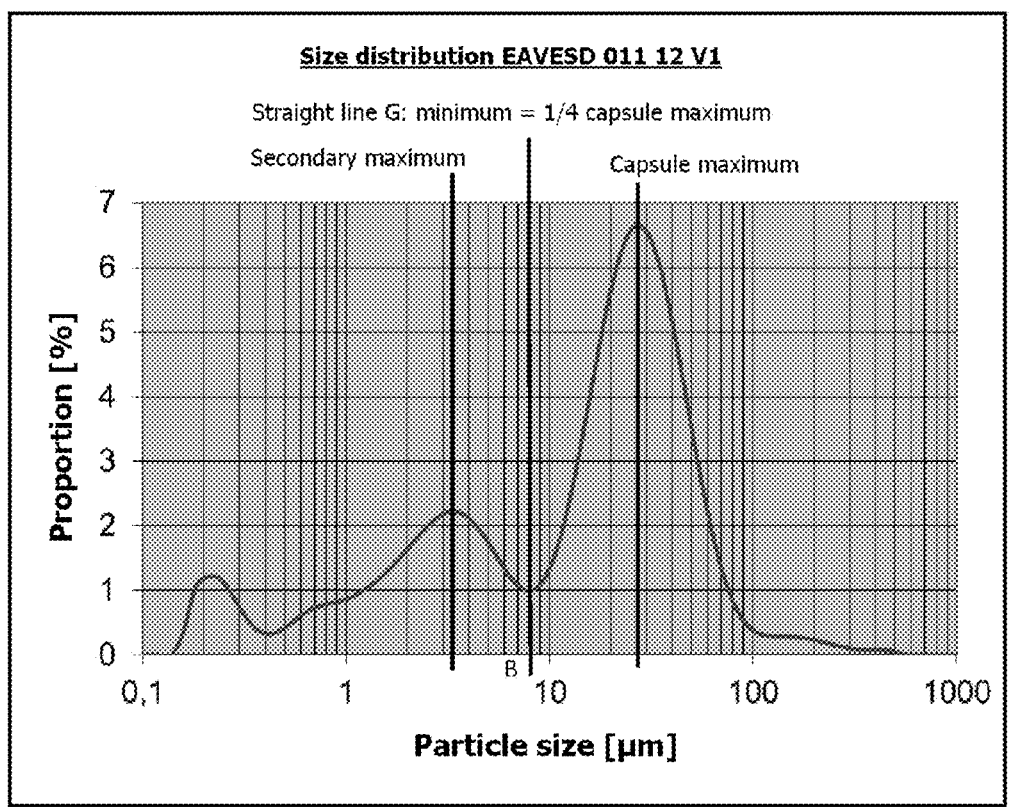

Figure 2 (Test1)
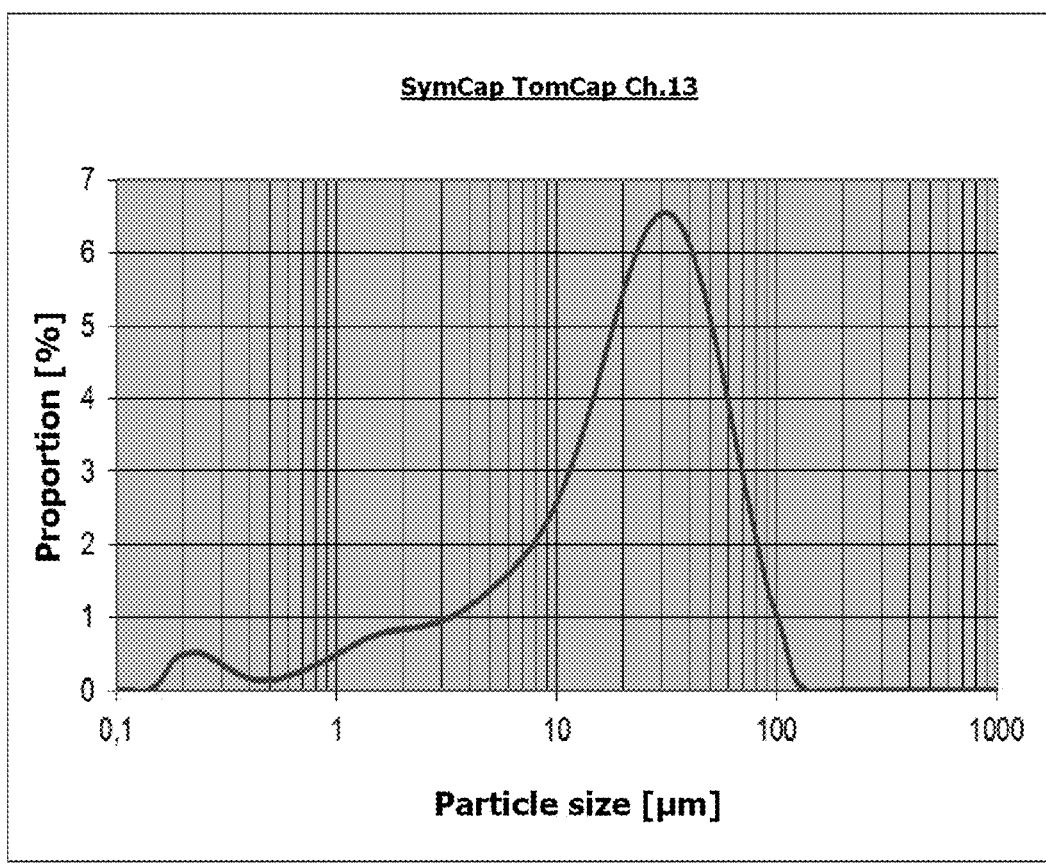

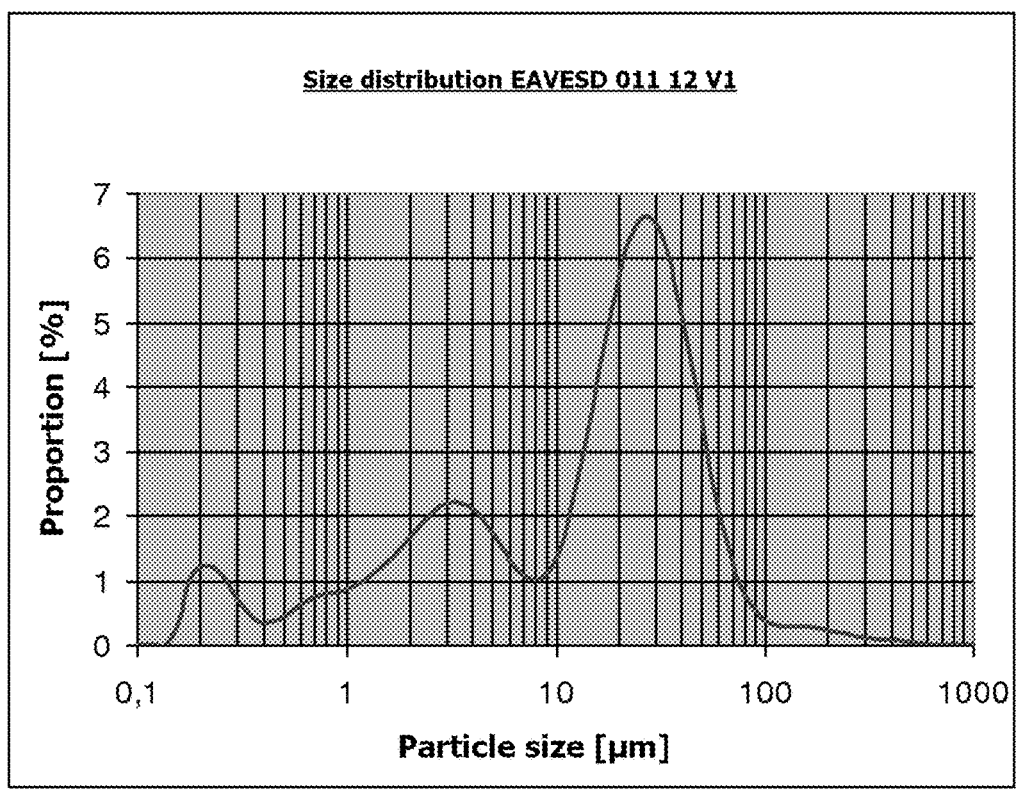
Figure 3 (Test 2-1)

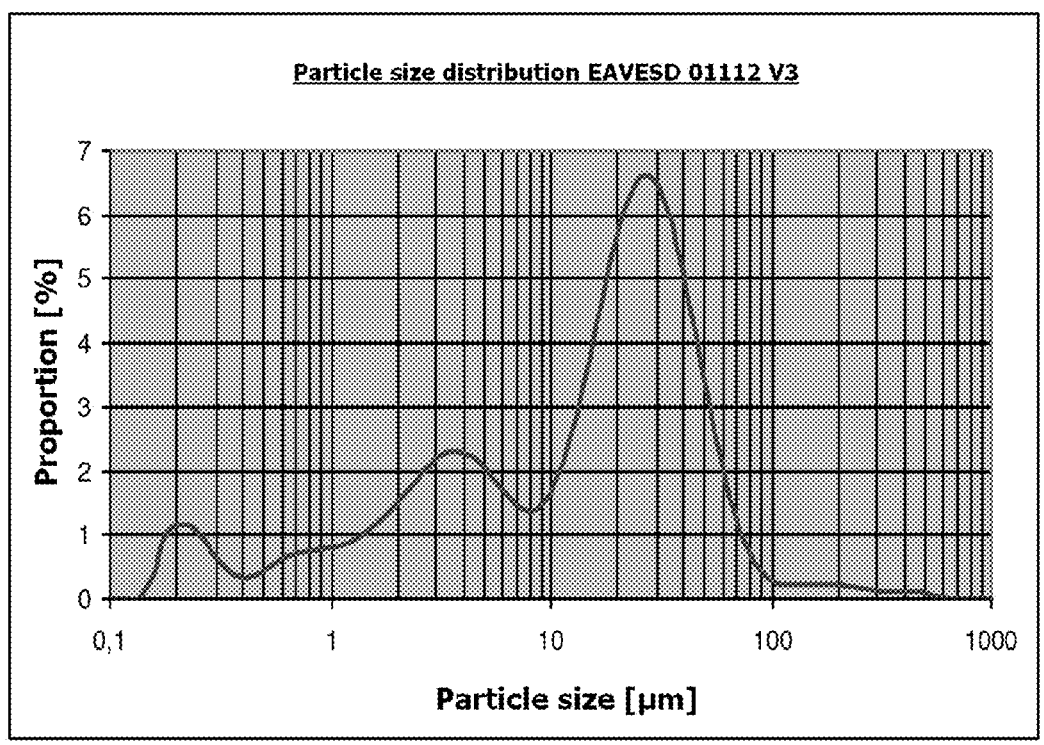
Figure 4 (Test 2-2)

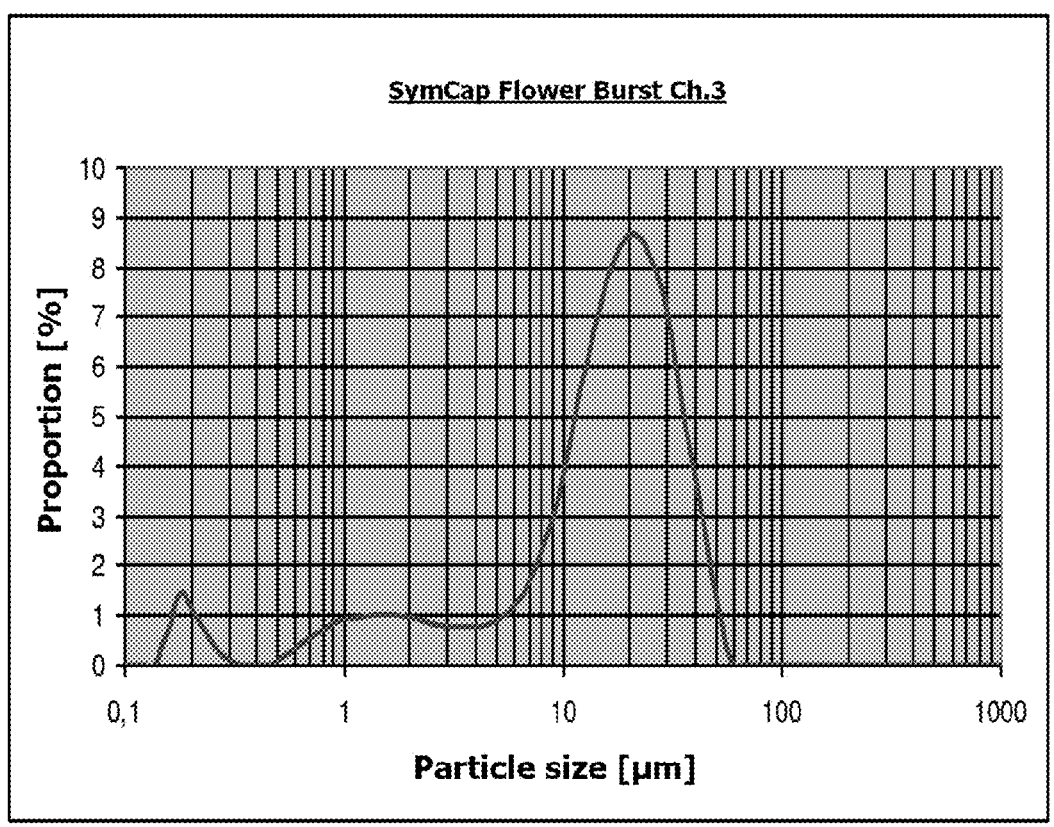
Figure 5 (Test 3)

Figure 6 (Test 4)
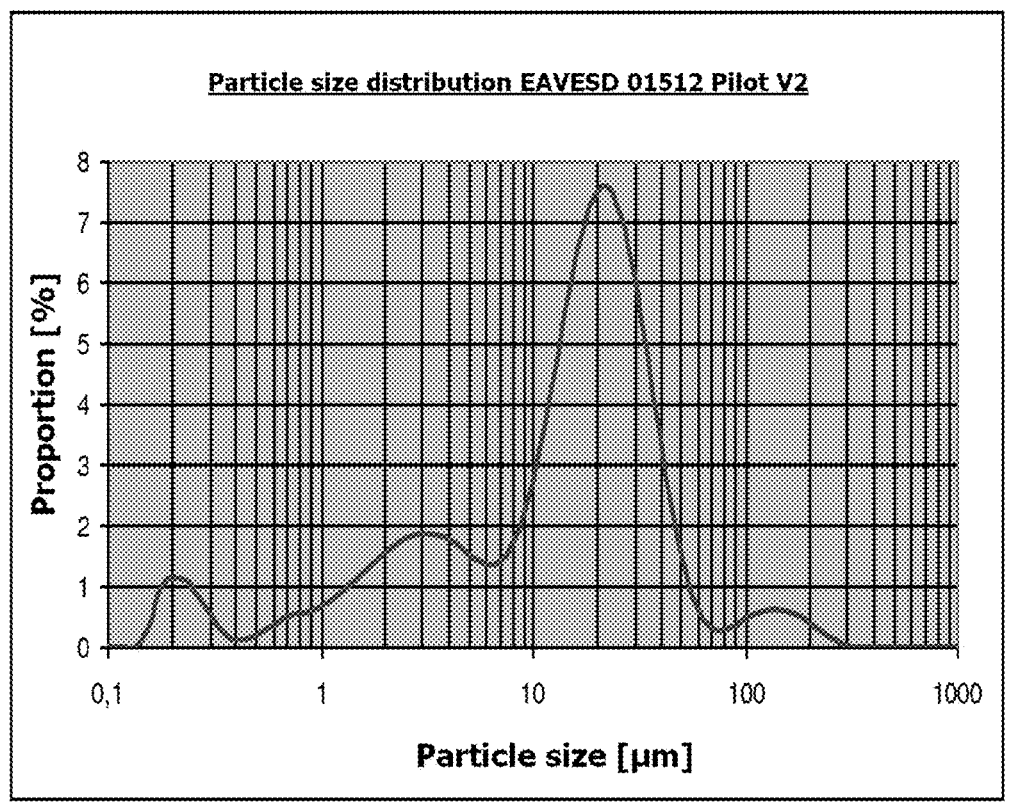

Figure 7 (Test 5)
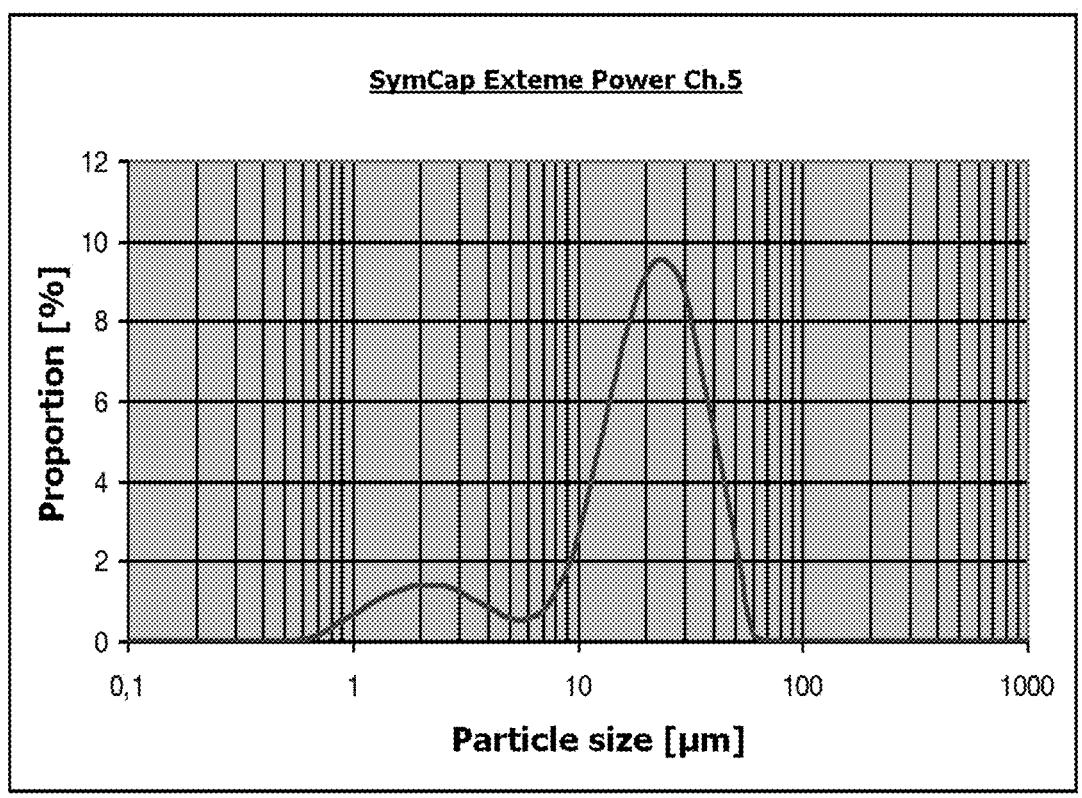

Figure 8 (Test 6)
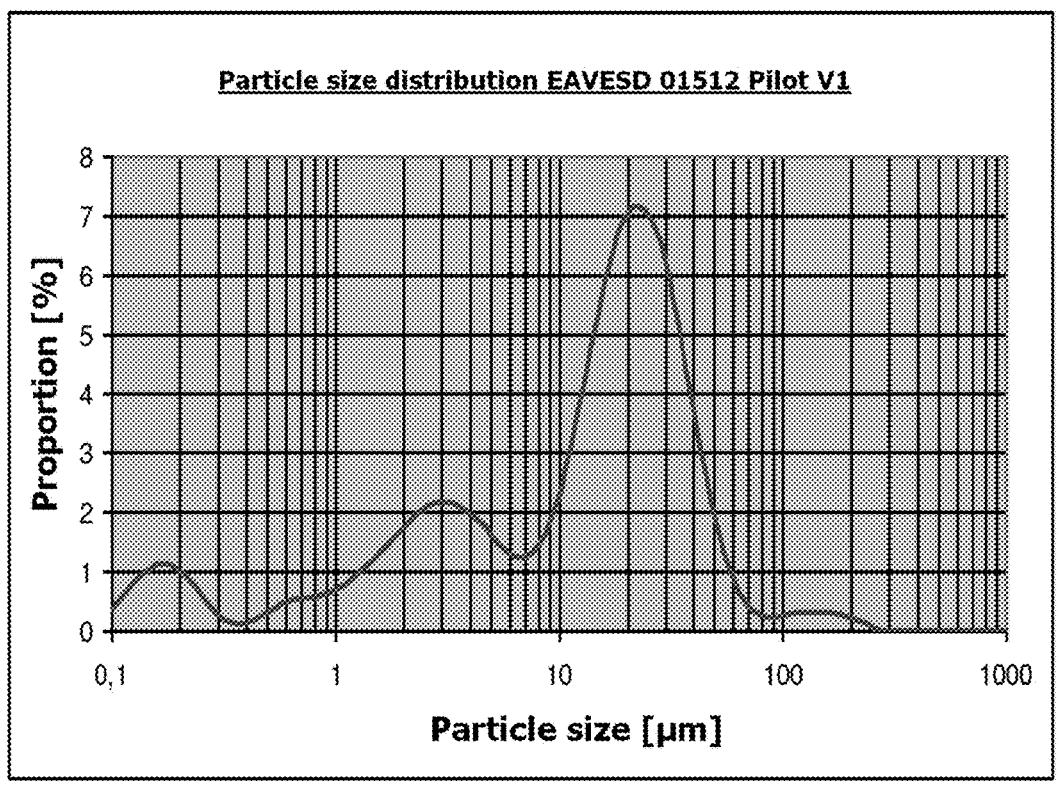

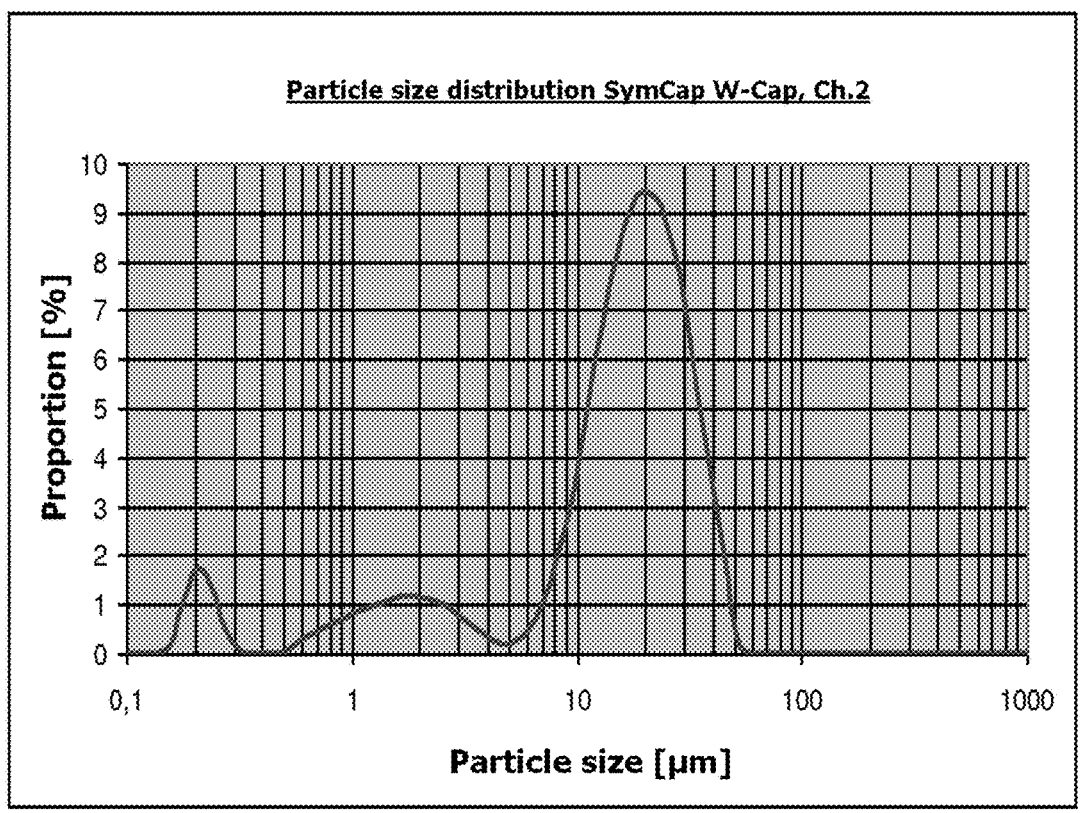
Figure 9 (Test 7)

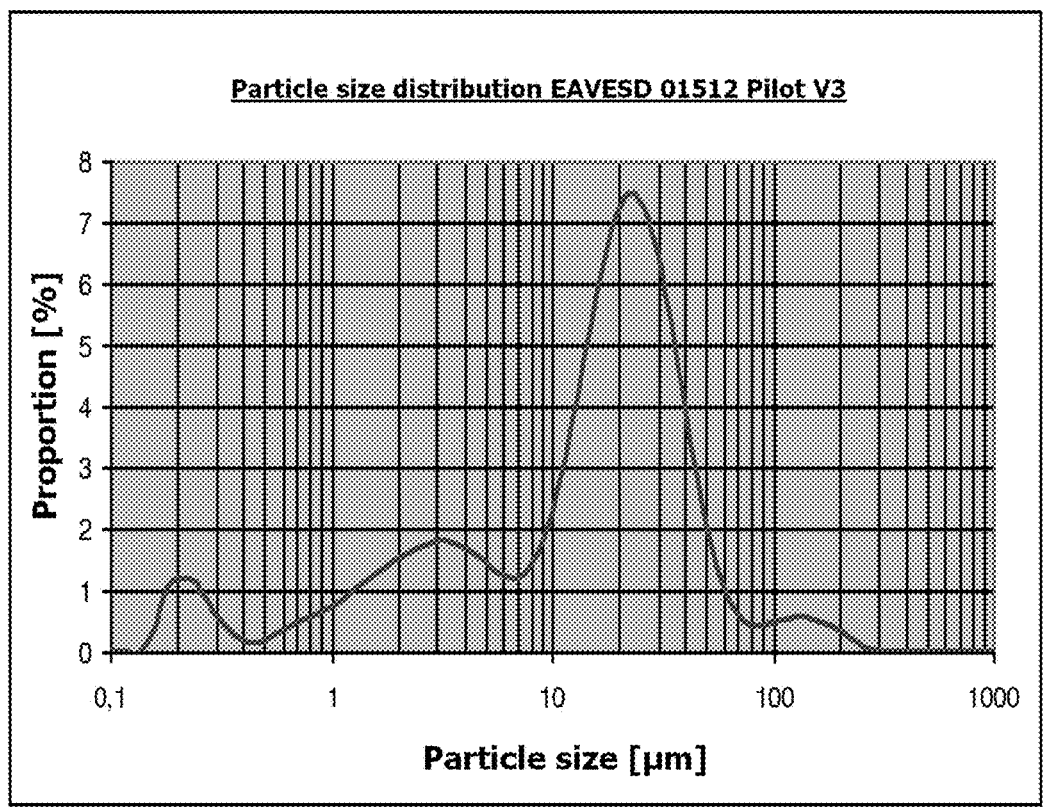
Figure 10 (Test 8)

Figure 11 (Example 1 Laboratory approach)
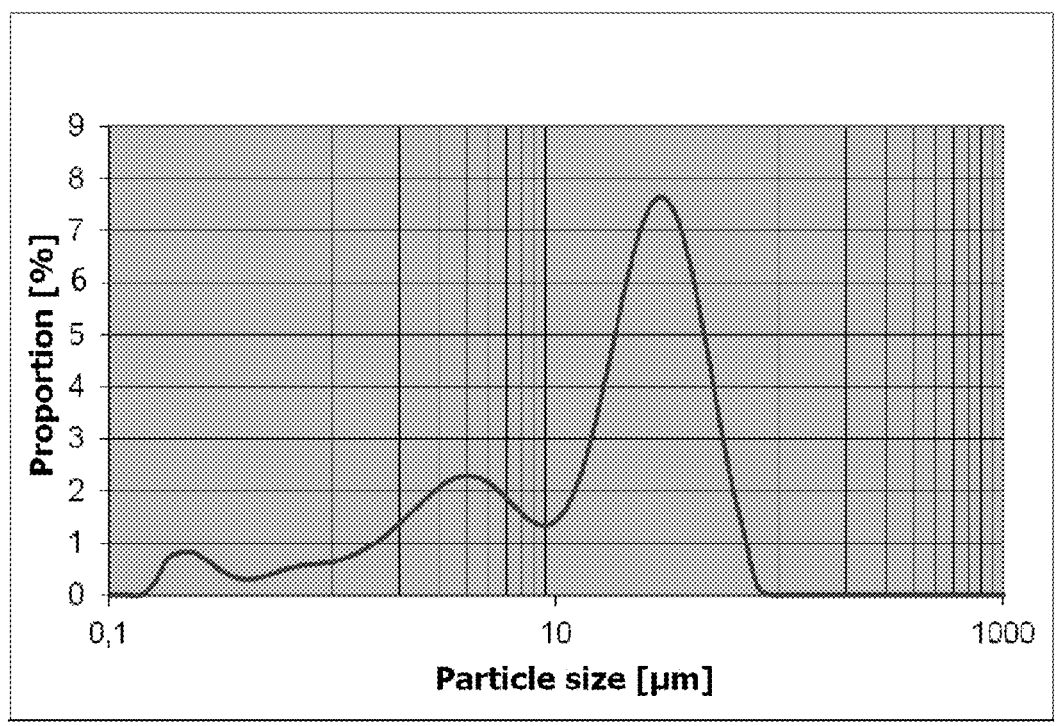

FRAGRANT OIL ENCAPSULATION

CROSS-REFERENCE TO RELATED APPLICATIONS

This application is a U.S. National Stage Entry of International Patent Application No. PCT/EP2013/65768, filed 25 Jul. 2013, which in turn claims priority to, and the benefit of, European Patent Application No. 12178132.2, filed 26 Jul. 2012, all of which are incorporated herein by reference in their entireties.

The present invention relates to microcapsules which are distinguished by a particularly favourable release characteristic behaviour of the core material enclosed in the microcapsules. The present invention relates furthermore to a suspension of such microcapsules in a liquid as well as the use thereof as a constituent of liquid laundry detergents, fabric softeners, cleaning agents, washing powders, shower gels, shampoos, deodorants and/or body lotions.

In many cases it is desirable that microcapsules release the constituent enclosed in the form of a hydrophobic core material under precisely defined conditions. Thus for example in the case of microcapsules which contain fragrant substances it is necessary that the microcapsules enclose the fragrances, which are generally very sensitive to oxidation, so that they are stable in storage and that only at the moment of the desired fragrance development the microcapsules are broken open by mechanical action.

Many articles of daily life, such as for example cleaning agents, fabric softeners, washing powders, liquid laundry detergents, shower gels, shampoos, deodorants, body lotions etc., are nowadays perfumed with aromatic substances or mixtures of aromatic substances. Interactions of the aromatic substances with other constituents of the formulation or premature evaporation of the lighter volatile components of a perfume occur very frequently. As a rule this leads to the olfactory impression of the perfume changing or vanishing completely.

The microencapsulation of such mixtures of aromatic substances offers the possibility of reducing or completely preventing interactions in the perfumed product or evaporation of the slightly volatile constituents.

Core/shell microcapsules are usually produced by the fine dispersion of the core material in an aqueous phase. Then in a coacervation process the wall material is precipitated out of the phase (aqueous phase) surrounding the drops of oil onto the drops of oil deposited. The size of the drops of oil therefore directly determines the size the subsequent capsule cores. In such coacervations aminoplasts are very frequently employed as wall material. These aminoplasts are very frequently based on the condensation of melamine and formaldehyde or other amine components or aldehydes. Methods for producing such microcapsules are sufficiently known.

Such microcapsules are already employed in liquid laundry detergents and fabric softeners. In this connection reference may be made here to the publications US 2010/40884 (Appleton); WO 2003/2699, WO 2006/121639, WO 2008/5693, US 2008/295256, US 2010/0279916 (Colgate Palmolive); WO 2006/131846 (Firmenich); Chimia 2011, 65, No. 3 177-181 (Bône et al.), WO 2008/98387, WO 2009/100553 (Givaudan); WO 2010/060677, WO 2010/28907, WO 2010/43452 (Henkel); EP 1797946, EP 1797947, US 2009/258042 (international Flavours and Fragrances); WO 2009/047745, WO 2010/114753 (Procter & Gamble); EP 2204155 (Takasago); WO 2011/120772 (Unilever).

This means that a fabric softener containing the capsule or a liquid laundry detergent containing the capsule should give the laundry treated therewith a longer-lasting fragrance than if the fragrant oil were freely present or should release a burst of fragrance when the laundry is rubbed or agitated. The capsules must remain in the textile fabric as much as possible and must break under mechanically loading and release the contained fragrant oil. The optimal correlation between capsule size and capsule stability are determined by practical application tests. The close cross-linking, such as is present for example in aminoplasts based on melamine and formaldehyde, is the cause of the high impermeability of this capsule wall in an aqueous medium containing surfactant (fabric softener, liquid laundry detergent).

It has been shown that the microcapsules proposed hitherto in the prior art do not have sufficient storage stability for many applications. In this connection reference is made to WO 01/49817, which describes microcapsule preparations, and describes the microcapsules with a core of a hydrophobic material which comprises at least one fragrant or aromatic substance.

In particular when such microcapsules with enclosed fragrant oils are used in liquid laundry detergents or fabric softeners it is observed that when this composition is stored over a relatively long period of time a considerable release of the fragrance occurs, which of course leads to a lesser release of fragrance at the desired site of action, specifically the washed laundry. Furthermore, in the microcapsules described hitherto in the prior art with encapsulation of fragrant oils it has been shown that fragrant substances cannot be released to the required extent by friction of the treated laundry.

Against this background the object of the present invention is to provide microcapsules which have a greater storage stability. In particular the object of the invention is to provide microcapsules which when stored in the form of liquid suspensions of the microcapsules, such as for example in washing agents or fabric softeners, experience a lesser release of the constituents, in particular in the form of fragrances. A further object of the present invention is to provide microcapsules with a hydrophobic fragrant oil as core material which after application to laundry exhibit favourable release characteristic behaviour of the fragrant oils when the treated laundry is rubbed.

A BRIEF DESCRIPTION OF THE DRAWINGS

FIG. 1 shows a graphical representation of the particle size of microcapsules plotted against the proportion of the respective particle size in percentage terms;
FIG. 2 shows particle size distribution for Test No. 1;
FIG. 3 shows particle size distribution for Test No. 2-1;
FIG. 4 shows particle size distribution for Test No. 2-2;
FIG. 5 shows particle size distribution for Test No. 3;
FIG. 6 shows particle size distribution for Test No. 4;
FIG. 7 shows particle size distribution for Test No. 5;
FIG. 8 shows particle size distribution for Test No. 6;
FIG. 9 shows particle size distribution for Test No. 7;
FIG. 10 shows particle size distribution for Test No. 7; and
FIG. 11 shows particle size distribution for Example 1, Laboratory approach.

The aforementioned object is achieved according to the invention by microcapsules with a volume-related particle size distribution has which the at least two maxima, wherein the main maximum of the particle size lies in the range from 5 to 100 µm and wherein the volume occupied by the microcapsules which have a particle size ≤one quarter of the particle size of the main maximum is ≥approximately 20% of the total volume of the microcapsules.

Thus a significant feature of the microcapsules according to the invention is the percentage volume ratio of the particle size ranges relative to one another.

This may be illustrated below with reference to FIG. 1:

FIG. 1 shows a graphical representation of the particle size of microcapsules plotted against the proportion of the respective particle size in percentage terms. In FIG. 1 the straight line G intersects the graph at point B at a quarter of the particle size of the main maximum. The capsule volume to the left of this point B is ≥approximately 20% of the total volume of all capsules. These volume ratios can be seen from the raw data of the volume percentages. What is more common is the reverse representation, wherein for example the median particle diameter is indicated, below which 90% of the particle volume is located, the so-called $d_{90}$ value.

Surprisingly it has been shown that laundry washed with liquid laundry detergents or fabric softener containing the capsules according to the invention exhibits a greater release of fragrance after friction than laundry washed with liquid laundry detergent or fabric softener containing the melamine formaldehyde capsules according to the prior art. With reference to the physical data such as capsule maximum, wall thickness and free oil content the capsules according to the invention do not differ significantly from the microcapsules of the prior art. Therefore it may be assumed that the particle size distribution is the cause of the improved release of fragrance.

However, it can be seen from the particle size distributions of the capsule dispersions according to the invention that they contain significantly more fine elements (small capsules and polymer powder) than the competing capsules. Most particle size distribution curves are bimodal. The curve minimum between the main maximum and the secondary maximum is defined as the boundary between the secondary peak (fine elements) and the main capsule peak. No significance is attached to the third peak in the extremely fine range which occurs with some capsule batches. If there is a minimum between the main and secondary peak, it is between 25% and 28.5% of the diameter of the main maximum. In order also in monomodal capsules to be able to draw a conclusion about the ratio of fine elements (small capsules and polymer powder) to the main capsule, the boundary is defined at a particle diameter between 25% and 28.5% of the curve maximum.

With the aid of a particle size measuring unit which takes individual photographs of all particles in a sample of which the diameter is determined and the data are evaluated statistically, it may be ascertained that the particles in the boundary region between the main and secondary maximum relate predominantly to microcapsules. Also the secondary maximum consists predominantly of microcapsules. The particle size of the so-called polymer powder which is produced as a by-product in this type of microencapsulation is located predominantly <3 µm. More precise statements about the quantitative ratio between small capsules and polymer powder cannot be made.

A precisely verifiable explanation of why a bimodality occurs in most particle size distribution curves is not known. A frequent explanation is that agglomeration processes of the small capsules lead to this. An oil emulsion before the encapsulation exhibits a substantially less pronounced bimodality in its particle size distribution curve.

Overall the mixture of large and small capsules, agglomerates and polymer powder which is typically present in the capsules according to the invention leads to a better action of the capsules in the end use applications. This is a stronger burst of fragrance after rubbing of an item of laundry treated with liquid laundry detergent or fabric softener containing the capsules according to the invention. Without wishing to be tied to a theory, the inventors surmise that the presence of smaller particles simplifies the breaking up of capsules containing a hydrophobic fragrant oil by rubbing of the laundry.

It is not possible to determine exactly quantitatively the amount of encapsulated fragrant oil in a washed item of laundry, the microcapsules suspended therein cannot be separated off quantitatively and the microcapsules cannot be disrupted quantitatively in the laundry.

In a particularly preferred embodiment the microcapsules according to the invention are characterised in that the volume occupied by the microcapsules which have a particle size of ¼ of the particle size of the main maximum is approximately 22%, in particular approximately 25% of the total volume of the microcapsules.

It has been shown that particularly good results are achieved when the microcapsules according to the invention are configured so that the main maximum of the particle size distribution is 10 to 50 µm, in particular 15 to 40 µm and a secondary maximum of the particle size distribution is 1 to 6 µm, in particular 1.5 to 4 µm, more preferably 2 to 3.5 µm.

In a particularly preferred embodiment the microcapsules according to the invention are configured so that the volume occupied by the microcapsules which have a particle size of ≤6 micrometers is ≥approximately 20% of the total volume of the microcapsules. In a particularly preferred embodiment the microcapsules according to the invention are configured so that the volume occupied by the microcapsules which have a particle size of ≤6 micrometers is ≥approximately 22%, in particular ≥approximately 25% of the total volume of the microcapsules.

In microcapsules the according to the invention any material which is suitable in order to form microcapsules can be used as capsule wall material. The capsule wall material of the microcapsules is preferably an aminoplast. In a particularly preferred embodiment the microcapsules according to the invention are configured so that the microcapsules have a capsule wall made of a methylated melamine-formaldehyde resin and/or urea-formaldehyde resin and/or reaction products of aldehydes with thiourea, N-alkylurea, guanidine, acetoguanamine, benzoguanamine, capronoguanamine, cyanamine, dicyandiamide and/or alkyl-/arylsulphonamide.

Any material which is suitable for inclusion in microcapsules may be considered as core material for the microcapsules according to the invention. The microcapsules according to the invention preferably have a core material made of at least one substantially water-insoluble material. In a particularly preferred embodiment the microcapsules according to the invention are configured so that the microcapsules have a core material which comprises a hydrophobic fragrant oil, a pesticide, a biocide, an insecticide, a substance from the group of repellents, a cosmetic active substance, a dye or mixtures of dyes, fluorescent colours, optical brighteners, solvents, waxes, silicone oils, lubricants, monomers for polymerisations or polycondensations, reactive synthetic materials, for example adhesives for single or multiple components, paint ingredients, flame retardants, pigment dispersions in organic solvents, aromatic substances and/or agrochemicals.

In a preferred embodiment the microcapsules according to the invention have a core material in the form of a hydrophobic fragrant oil, wherein this core material contains one or more aromatic substances selected from the group consisting of:

extracts of natural raw materials such as essential oils, concretes, absolutes, resins, resinoids, balsams, tinctures such as e.g. ambergris tincture; amyris oil; angelica seed oil; angelica root oil; anise oil; valerian oil; basil oil; tree moss absolute; bay oil; mugwort oil; benzoin resin; bergamot oil; beeswax absolute; birch tar oil; bitter almond oil; summer savory oil; buchu oil; cabreuva oil; oil of cade; calamus oil; camphor oil; cananga oil; cardamom oil; cascarilla oil; oil of cassia; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill oil; dill seed oil; eau de brouts absolute; oak moss absolute; elemi oil; tarragon oil; Eucalyptus citriodora oil; eucalyptus oil; fennel oil; spruce-needle oil; galbanum oil; galbanum resin; geranium oil; grapefruit oil; guaiacwood oil; gurjun balsam; gurjun balsam oil; helichrysum absolute; helichrysum oil; ginger oil; orris root absolute; orris root oil; jasmine absolute; calamus oil; blue camomile oil; Roman camomile oil; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linaloa oil; litseacubeba oil; oil of laurel leaves; oil of mace; marjoram oil; mandarin oil; massoia bark oil; mimosa absolute; musk seed oil; musk tincture; oil of clary sage; nutmeg oil; myrrh absolute; myrrh oil; myrtle oil; clove leaf oil; clove flower oil; Neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; oil of petitgrain; peppermint oil; pepper oil; pimento oil; pine oil; poley oil; rose absolute; rosewood oil; rose oil; rosemary oil; oil of Dalmatian sage; oil of Spanish sage; sandalwood oil; celery seed oil; spike oil; star anise oil; styrax oil; tagetes oil; fir-needle oil; tea tree oil; terpentine oil; thyme oil; tolu balsam; tonka absolute; tuberose absolute; vanilla extract; violet leaf absolute; verbena oil; vetiver oil; oil of juniper berries; grapeseed oil; vermouth oil; oil of wintergreen; ylang oil; oil of hyssop; civet absolute; cinnamon leaf oil; cinnamon bark oil as well as fractions thereof, or ingredients isolated therefrom;

individual fragrances from the group of hydrocarbons, such as for example 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic aldehydes and acetals thereof, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyloxyacetaldehyde; 1-(1-methoxy-propoxy)-(E/Z)-3-hexene;

aliphatic ketones and their oximes, such as for example 2-heptanone; 2-octanone; 3-octanone; 2-nonanone; 5-methyl-3-heptanone; 5-methyl-3-heptanoneoxime; 2,4,4,7-tetramethyl-6-octen-3-one; 6-methyl-5-hepten-2-one;

aliphatic sulphur-containing compounds, such as for example 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles, such as for example 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

esters of aliphatic carboxylic acids, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl (E,Z)-2,4-decadienoate; in particular ethyl-2-trans-4-cis-decadienoate; methyl 2-octinate; methyl 2-noninate; allyl 2-isoamyloxyacetate; methyl 3,7-dimethyl-2,6-octadienoate; 4-methyl-2-pentyl-crotonate;

formates, acetates, propionates, isobutyrates, butyrates, isovalerates, pentanoates, hexanoates, crotonates, tiglinates or 3-methyl-2-butenoates of acyclic terpene alcohols, such as for example citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol;

acyclic terpenealdehydes and ketones, such as for example geranial; neral; citronellal; 7-hydroxy-3,7-dimethyloctanal; 7-methoxy-3,7-dimethyloctanal; 2,6,10-trimethyl-9-undecenal; geranylacetone; and the dimethyl- and diethyl-acetals of geranial, neral, 7-hydroxy-3,7-dimethyloctanal;

formates, acetates, propionates, isobutyrates, butyrates, isovalerates, pentanoates, hexanoates, crotonates, tiglinates, 3-methyl-2-butenoates of cyclic terpene alcohols, such as for example menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol;

cyclic terpenealdehydes and ketones, such as for example menthone; isomenthone; 8-mercaptomenthan-3-one; carvone; camphor; fenchone; alpha-ionone; beta-ionone; alpha-n-methyl ionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexene-1-yl)-2-butenale; nootcatone; dihydronootcatone; 4,6,8-Megastigmatriene-3-one; alpha-sinensal; beta-sinensal; acetylated cedar wood oil (methyl cedryl ketone);

cyclic and cycloaliphatic ethers, such as for example cineol; cedryl methyl ether; cyclododecyl methyl ether;

1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.10.0]-trideca-4,8-diene; rose oxide; 2-(2,4-dimethyl-3-cyclohexen-1-yl)-5-methyl-5-(1-methylpropyl)-1,3-dioxane;

cyclic and macrocyclic ketones, such a, for example 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclohexanone; 4-tert.-pentyl-cyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cyclo-heptadecen-1-one; cyclopentadecanone; cyclohexadecanone;

cycloaliphatic aldehydes, such as for example 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

cycloaliphatic ketones, such as, for example, 1-(3,3-dimethylcyclohexyl)-4-penten-1-1-cyclohexen-1-yl)-4-penten-1-one; 2,3,8,8-tetra-methyl-1,2,3,4,5,6,7,8-octahydro-2-naphthalenyl methyl ketone; methyl 2,6,10-trimethyl-2,5,9-cyclododecatrienyl ketone; tert.-butyl (2,4-dimethyl-3-cyclohexen-1-yl) ketone;

esters of cyclic alcohols, such as, for example, 2-tert-butyl cyclohexylacetate; 4-tert-butyl cyclohexylacetate; 2-tert-pentyl cyclohexylacetate; 4-tert-pentyl cyclohexylacetate; 3,3,5-trimethylcyclohexylacetate; decahydro-2-naphthyl acetate; 2-cyclopentyl-cyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

esters of cycloaliphatic alcohols such as for example 1-cyclohexylethylcrotonate;

esters of cycloaliphatic carboxylic acids, such as, for example, allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexene-carboxylate; ethyl 2-methyl-1,3-dioxolan-2-acetate;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, such as, for example, 2-phenylethyl methyl ether; 2-phenylethyl isoamyl ether; 2-phenylethyl 1-ethoxyethyl ether; phenylacetaldehydedimethylacetal; phenylacetaldehyde-diethylacetal; hydratropaaldehydedimethylacetal; phenylacetaldehydeglycerinacetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

aromatic and araliphatic aldehydes, such as, for example, benzaldehyde; phenylacetaldehyde; 3-phenylpropanal; hydratropaaldehyde; 4-methyl-benzaldehyde; 4-methylphenylacetaldehyde; 3-(4-ethylphenyl)-2,2-dimethyl-propanal; 2-methyl-3-(4-isopropylphenyl)propanal; 2-methyl-3-(4-tert.-butyl-phenyl)propanal; 2-methyl-3-(4-isobutylphenyl)propanale; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxy-benzaldehyde; 3,4-dimethoxybenzaldehyde; 2-methyl-3-(4-methoxyphenyl)-propanal; 2-methyl-3-(4-methylenedioxyphenyl)propanal;

aromatic and araliphatic ketones, such as, for example, acetophenone; 4-methylacetophenone; 4-methoxyacetophenone; 4-tert.-butyl-2,6-dimethyl-acetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl) ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and their esters, such as, for example, benzoic acid; phenylacetic acid; methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert.-butylbenzene; 3,5-dinitro-2,6-dimethyl-4-tert.-butylacetophenone; cinnamic acid nitrile; 5-phenyl-3-methyl-2-pentenoic acid nitrile; 5-phenyl-3-Schiff's Schiff's bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; indole; scatole; 2-methoxy-3-isopropylpyrazine; 2-isobutyl-3-methoxypyrazine;

phenyl ethers and phenyl esters, such as, for example, estragole; anethole; eugenyl methyl ether; isoeugenyl methyl ether; diphenyl ether; beta-naphthyl methyl ether; beta-naphthyl ethyl ether; beta-naphthyl isobutyl ether; 1,4-dimethoxybenzene; eugenyl acetate; p-cresylphenyl acetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

dihydrocoumarin; octahydrocoumarin; lactones, such as, for example, 1,4-octanolide; 3-methyl-1,4-octanolide;

1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecane dioate; ethylene-1,13-tridecane dioate; coumarin; 2,3-dihydrocoumarin; octahydrocoumarin.

A criterion which is important for the usability of the microcapsules is the weight ratio of core material to capsule wall material. Whereas on the one hand the largest possible proportion of core material is sought, in order to facilitate the highest possible useful value of the capsules, on the other hand it is necessary that the capsules still have a sufficient proportion of capsule wall material so that the stability of the capsules is ensured.

According to the invention it has proved particularly advantageous, that the microcapsules are configured so that the microcapsules have a weight ratio of core material to capsule wall material which is approximately 50-90 to 50-10, in particular approximately 70-80 to 30-20.

A particularly suitable form of the use of the microcapsules according to the invention consists of admixing it with the end product in the form of a suspension. Therefore the present invention also relates to a suspension of the microcapsules described above in a liquid, in particular in water. Such a suspension has particularly advantageous characteristics when it is configured so that the proportion by weight of the microcapsules is approximately 20 to 60% by weight, in particular approximately 25 to 50% by weight, more preferably approximately 30 to 35% by weight.

In order to prevent mixing of such a suspension and thus to achieve a high storage stability, it has proved advantageous that the suspension has a viscosity of 12 to 1500 mPas. In order to obtain the required viscosity of the suspension a thickening agent is preferably employed.

The microcapsules according to the invention are particularly suitable for enclosing hydrophobic fragrant oils, which can then be used in various cleaning products.

Thus the present invention also relates in particular to the use of the described microcapsules as a constituent of liquid laundry detergents, fabric softeners, cleaning agents, washing powders, shower gels, shampoos, deodorants and/or body lotions.

In a preferred embodiment the use takes place so that in the suspension as described above of the microcapsules according to the invention in a liquid first of all the water is extracted in particular by spray-drying and the microcapsules thus dried are added to the product.

In order to be able to determine the particle size distribution of microcapsules, and to be able determine therefrom the ratios of the size ranges of the particles, the following method is employed within the context of the present invention: The measurement of the particle size distribution took place with the aid of laser diffractometry. For this purpose a Mastersizer 2000 (Malvern Instruments, Worcestershire, UK) was used, which is equipped with a fluid dispersion unit Hydro 2000SM. The dispersion unit has a mechanical stirrer.

For the measurement a sufficient quantity of the sample was dispersed in water with the aid of the dispersion unit and measured.

The raw data were then evaluated with the aid of the software Mastersizer 2000 Version 5.54 which is also supplied. The Mie theory is used by this software as optical model for determination of the particle size.

It has been shown that the use from microcapsules according to the invention, in which hydrophobic fragrant oils are encapsulated, leads to significant advantages over the microcapsules known from the prior art. This was also shown in particular by sensor-based tests conducted on laundry which has been treated with microcapsules containing fragrant substances according to the present invention or with microcapsules from the prior art in the form of a fabric softener or a liquid laundry detergent formulation containing the microcapsules. In the sensor-based evaluation an odour evaluation of the item of laundry was carried out without and with rubbing and with a grading scale.

The invention described above is explained in further detail below with reference to examples.

EXAMPLE 1

Production of a Microcapsule According to the Invention

In a cylindrical 1 liter beaker 28.95 g of a 40% solution of a sulphonated melamine-formaldehyde precondensate (for example: Melapret AAS 40 M, melamine kemična tovarna d.d., Kočevje) are diluted at approximately 22° C. with 146.50 g water. While stirring with a high-speed stirrer (IKA Eurostar power control-visc 6000 with stirrer tool R1402 (dissolver disc with precision shaft) at 2400 U/min, 32.47 g of an aqueous solution of a cationised melamine-formaldehyde precondensate (for example Melapret KMS 30 N, from melamine kemična tovarna d.d., Kočevje), which has been obtained by dissolving 7.90 g of a 30% solution thereof in 24.57 g water are added followed by stirring for 30 s. Immediately thereafter, without interruption of the stirring and still with stirring at 2400 U/min, this solution at approximately 22° C. has added to it 190.09 g of a non-water-miscible fragrant oil (for example Tomcap, from Symrise) likewise at 22° C. and emulsified for 30 minutes. A stable oil-in-water-emulsion is obtained, of which the average particle size of approximately 20 μm is determined by means of laser diffraction (Coulter LS 230, optical model according to Fraunhofer or Malvern Mastersizer 2000 m optical model according to Mie). The emulsion is transferred to a closed 1 liter 4-necked flask with paddle mixer and reflux condenser, which is temperature-controlled in a water bath at 30° C. Then whilst continuing stirring 7.44 g of a 20.5% formic acid are added, wherein a pH value of approximately 3.8 is set. To these emulsion gives man 73 g of a 41.0% solution of a methylated melamine-formaldehyde precondensate (wall-forming resin, for example: Melapret NF 70 M, from Melamin kemična tovarna d.d., Kočevje) are added to this emulsion and heated within 15 minutes to 60° C. The stirring speed should be adapted so that good intermixing is ensured. When 60° C. is reached the mixture is diluted with 57.60 g. After a further 15 minutes 21.32 g of wall-forming resin are added. Subsequently by addition of 20.5% formic acid the pH value is again set to the value measured before the addition. Stirring of the batch is continued for 3.5 hours at 60° C. After the 4-hour reaction time is ended the heating of the water is switched off and the dispersion is cooled whilst being stirred at room temperature. By the addition of 4 g of 12.5% ammonia solution the pH value is set to 8.5 and as a result lowers the content of free formaldehyde to below 1500 ppm.

A capsule dispersion is obtained with a bimodal (strictly speaking trimodal) particle size distribution curve (FIG. 11)

and an average particle size of 20.1 μm (D(4,3)-Wert, Malvern Mastersizer 2000). The proportion of fines in this capsule amounts to 30.1% according to the procedure illustrated in FIG. 1.

II Description of the Sensor-Based Test for Evaluation of the Capsules

Composition of Liquid Laundry Detergent:

For sensor-based evaluation of the capsules the dispersions with a perfume oil content of approximately 25% were incorporated into a liquid laundry detergent formulation (approximately 29% active washing substances) in a concentration of 0.2%. Then in a commercially available European washing machine 2 kg of laundry were washed with 40 g of this formulation.

Composition of Fabric Softener:

For sensor-based evaluation of the capsules the dispersions with a perfume oil content of approximately 25% were incorporated into a fabric softener formulation (approximately 15% active washing substances) in a concentration of 0.2%. Then in a commercially available European washing machine 2 kg of laundry were washed with 20 g of this formulation.

Carrying Out the Sensor-Based Evaluation:

For sensor-based evaluation the samples were anonymised and each sample was presented twice. In each case a maximum of 4 samples were evaluated simultaneously. The first sample was always unperfumed. A further unperfumed sample was among the anonymised samples. The panel of experts consisted of a minimum of 12 subjects.

The odour evaluation is performed on the item of laundry without and with rubbing and is evaluated according to a grading scale (the higher the number, the more intense the perceptible fragrance is).

III Comparison of Microcapsules According to the Invention with Microcapsules According to the Prior Art A series of tests were conducted in which microcapsules according to the invention are compared with regard to the relevant characteristics with microcapsules such as are described in the prior art.

For this purpose in Examples 2, 4, 6, 8 and 10 capsules according to the invention were produced with various hydrophobic fragrant oils. Examples 1, 3, 5 and 7 are comparative examples for which commercially available microcapsules with the same encapsulated fragrant oils were used. In this case the following commercially available capsules were used:

Symcap® Tomcap FS ST (Mat. No.: 338550)
Symcap® Fruit Rush FS ST (Mat. No.: 359173), contains capsule oil W-Cap
Symcap® Tomcap FS ST (Mat. No.: 338698)
Symcap Flower Burst FS ST (Mat. No.: 609818)
(Capsules sold by Symrise AG, 37603 Holzminden, Germany)

The fragrant oils which have been encapsulated are likewise commercially available from Symrise AG, 37503 Holzminden, Germany.

1) Capsule oil Tomcap (Mat. No.: 266485), comparative example
2) Capsule oil Tomcap (Mat. No.: 266485), microcapsule according to the invention
3) Capsule oil Flowercap (Mat. No.: 369892), comparative example
4) Capsule oil Flowercap (Mat. No.: 369892), microcapsule according to the invention
5) Capsule oil Extreme Power (Mat. No.: 229831), comparative example
6) Capsule oil Extreme Power (Mat. No.: 229831), microcapsule according to the invention
7) Capsule oil W-Cap (Mat. No. 358653), comparative example
8) Capsule oil W-Cap (Mat. No. 358653), microcapsule according to the invention In order to be able to compare the microcapsules of the prior art with the capsules according to the invention, they were in each case characterised with regard to capsule diameter, capsule wall thickness and particle size distribution characterises and subjected to sensor-based tests. The result is set out in the following Table 1:

TABLE 1

| | | Test No. | | | | | | | | |
|---|---|---|---|---|---|---|---|---|---|---|
| | | 1 | 2-1 | 2-2 | 3 | 4 | 5 | 6 | 7 | 8 |
| Capsule diameter* | μm | 26.0 | 23.3 | 22.9 | 17.0 | 20.9 | 19.8 | 18.6 | 16.8 | 21.5 |
| **Capsule wall thickness | nm | 260-350 | 130-180 | 170-200 | — | — | — | — | — | — |
| Capsule maximum | μm | 28.5 | 26.5 | 26.5 | 20.1 | 20.1 | 21.6 | 21.6 | 18.9 | 21.6 |
| Secondary maximum | μm | — | 3.1 | 3.6 | — | 2.9 | 2.0 | 2.9 | 1.7 | 2.9 |
| Fine elements (limit 1/4 of the maximum) | % | 18.8 | 33.0 | 32.8 | 17.3 | 25.2 | 14.2 | 29.7 | 16.7 | 25.6 |
| Fine elements limit 1/3.5 of the maximum) | % | 20.7 | 33.0 | 32.8 | 17.3 | 25.2 | 14.7 | 31.0 | 16.9 | 26.8 |
| Free fragrant oil | % | 0.15 | 0.14 | 0.13 | 0.19 | 0.11 | 0.05 | 0.06 | 0.13 | 0.10 |
| Sensor test in fabric softener without rubbing | Score | 0.08 | 0.28 | 0.17 | — | — | 0.12 | 0.09 | — | — |
| Sensor test in fabric softener after rubbing | Score | 3.54 | 3.88 | 3.85 | — | — | 2.43 | 2.81 | — | — |
| Sensor test in liquid laundry detergent without rubbing | Score | 0.03 | 0.29 | 0.12 | 0.86 | 0.25 | 0.06 | 0.11 | 0.25 | 0.10 |
| Sensor test in liquid laundry detergent after rubbing | Score | 2.7 | 3.19 | 3.18 | 3.50 | 3.71 | 2.86 | 2.78 | 3.09 | 3.58 |
| Free fragrant oil after 1 week at 40° C. in fabric softener | % | 5.5 | 4 | 4 | 13.2 | 3.2 | 7 | 1 | 8.2 | 4.5 |
| Sensor test in fabric softener without rubbing | Score | 0.15 | 0.63 | 0.32 | — | — | 0.40 | 0.14 | — | — |
| Sensor test in fabric softener after rubbing | Score | 2.17 | 3.80 | 3.59 | — | — | 1.69 | 2.76 | — | — |
| Free fragrant oil after 1 week | % | 10 | 2 | 2 | — | 1.7 | — | 0.75 | — | 1.5 |

TABLE 1-continued

| | | Test No. | | | | | | | | |
|---|---|---|---|---|---|---|---|---|---|---|
| | | 1 | 2-1 | 2-2 | 3 | 4 | 5 | 6 | 7 | 8 |
| at 40° C. in liquid laundry detergent | | | | | | | | | | |
| Sensor test in liquid laundry detergent without rubbing | Score | 0.08 | 0.38 | 0.17 | 0.39 | 0.32 | 0.13 | 0.03 | 0.13 | 0.09 |
| Sensor test in liquid laundry detergent after rubbing | Score | 2.29 | 3.64 | 3.07 | 2.71 | 3.39 | 2.13 | 2.91 | 2.91 | 3.56 |

*Mastersizer 2000, D(4,3) value, volume-related mean value
**determination by means of scanning electron microscopy of capsules which were destroyed at low temperatures (cyobreak process), by the Fraunhofer-Institut IAP, Potsdam-Golm.

The particle size distribution for Examples 1 to 8 is shown in FIGS. 2 to 10.

The invention claimed is:

1. Microcapsules with a particle size distribution which has at least two maxima, wherein the main maximum of the particle size distribution lies in the range of 10 to 50 μm, and a secondary maximum of the particle size distribution lies in the range of 1 to 6 μm, and wherein the volume occupied by the microcapsules which have a particle size ≤¼ of the particle size of the main maximum is ≥approximately 20% of the total volume of the microcapsules.

2. Microcapsules according to claim 1, wherein the volume occupied by the microcapsules which have a particle size of ≤¼ the particle size of the main maximum is ≥approximately 22% of the total volume of the microcapsules.

3. Microcapsules according to claim 1, wherein the volume occupied by the microcapsules which have a particle size of ≤6 micrometers is ≥approximately 20% of the total volume of the microcapsules.

4. Microcapsules according to, wherein the microcapsules have a capsule wall made of an aminoplast.

5. Microcapsules according to, wherein the microcapsules have a capsule wall made of a methylated melamine-formaldehyde resin and/or urea-formaldehyde resin and/or reaction products of aldehydes with thiourea, N-alkylurea, guanidine, acetoguanamine, benzoguanamine, capronoguanamine, cyanamine, dicyandiamide and/or alkyl-/arylsulphonamide.

6. Microcapsules according to claim 1, wherein the microcapsules have a core material made of at least one substantially water-insoluble material.

7. Microcapsules according to claim 1, wherein the microcapsules have a core material which comprises a hydrophobic fragrant oil, a pesticide, a biocide, an insecticide, a substance from the group of repellents, a cosmetic active substance, a dye or mixtures of dyes, fluorescent colours, optical brighteners, solvents, waxes, silicone oils, lubricants, monomers for polymerisations or polycondensations, reactive synthetic materials, for example adhesives for single or multiple components, paint ingredients, flame retardants, pigment dispersions in organic solvents, aromatic substances and/or agrochemicals.

8. Microcapsules according to claim 1, wherein the microcapsules have a weight ratio of core material to capsule wall material which is approximately 50-90 to 50-10.

9. A suspension of microcapsules according to claim 1 in a liquid.

10. The suspension of microcapsules according to claim 9, wherein the proportion by weight of the microcapsules is approximately 20 to 60% by weight.

11. The suspension according to claim 9, wherein the suspension has a viscosity in the range from 12 to 1500 mPas.

12. A product comprising microcapsules according to claim 1.

13. A product comprising microcapsules obtained from the suspension of microcapsules according to claim 9 with prior removal of the liquid therefrom.

14. The microcapsules according to claim 1, wherein the volume occupied by the microcapsules which have a particle size of ≤¼ of the particle size of the main maximum is approximately ≥25% of the total volume of the microcapsules.

15. The microcapsules according to claim 1, wherein the main maximum of the particle size distribution is 10 μm to 50 μm and a secondary maximum of the particle size distribution is 1.5 μm to 4 μm.

16. The microcapsules according to claim 1, wherein the main maximum of the particle size distribution is 10.mu.m to 50.mu.m and a secondary maximum of the particle size distribution is 2.mu.m to 3.5.mu.m.

17. The microcapsules according to claim 1, wherein the main maximum of the particle size distribution is 15 μm to 40 μm and a secondary maximum of the particle size distribution is 1 μm to 6 μm.

18. The microcapsules according to claim 1, wherein the main maximum of the particle size distribution is 15 μm to 40 μm and a secondary maximum of the particle size distribution is 1.5 μm to 4 μm.

19. The microcapsules according to claim 1, wherein the main maximum of the particle size distribution is 15 μm to 40 μm and a secondary maximum of the particle size distribution is 2 μm to 3.5 μm.

20. The microcapsules according to claim 1, wherein the volume occupied by the microcapsules which have a particle size of ≤6 micrometers is ≥approximately 22% of the total volume of the microcapsules.

21. The microcapsules according to claim 1, wherein the microcapsules have a weight ratio of core material to capsule wall material which is approximately 70-80 to 30-20.

22. The suspension of microcapsules according to claim 9, wherein the proportion by weight of the microcapsules is approximately 25 to 50% by weight.

23. The suspension of microcapsules according to claim 9, wherein the proportion by weight of the microcapsules is approximately 30 to 35% by weight.

24. The product of claim 12, wherein the product is selected from the group consisting of liquid laundry detergent, fabric softeners, cleaning agents, washing powders, shower gels, shampoos, deodorants and body lotions.

25. The product of claim 13, wherein the product is selected from the group consisting of liquid laundry detergent, fabric softeners, cleaning agents, washing powders, shower gels, shampoos, deodorants and body lotions.

* * * * *

UNITED STATES PATENT AND TRADEMARK OFFICE
CERTIFICATE OF CORRECTION

| | | |
|---|---|---|
| PATENT NO. | : 9,719,058 B2 | Page 1 of 1 |
| APPLICATION NO. | : 14/416212 | |
| DATED | : August 1, 2017 | |
| INVENTOR(S) | : Ralf Bertram et al. | |

It is certified that error appears in the above-identified patent and that said Letters Patent is hereby corrected as shown below:

On the Title Page

In item (71), Line 1, delete "AG" and insert --SE--.

In item (73), Line 2, delete "Holzminden" and insert --Oberkirch--.

In item (73), after Line 2, please add --SYMRISE AG, Holzminden (DE)--.

Signed and Sealed this
Twenty-third Day of October, 2018

Andrei Iancu
*Director of the United States Patent and Trademark Office*